United States Patent [19]
During

[11] Patent Number: 6,110,456
[45] Date of Patent: Aug. 29, 2000

[54] ORAL DELIVERY OR ADENO-ASSOCIATED VIRAL VECTORS

[75] Inventor: Mathew John During, Weston, Conn.

[73] Assignee: Yale University, New Haven, Conn.

[21] Appl. No.: 08/481,708

[22] Filed: Jun. 7, 1995

[51] Int. Cl.[7] ................................................... A61K 48/00
[52] U.S. Cl. .......................................... 424/93.2; 514/44
[58] Field of Search ........................... 514/44; 435/172.3, 435/320.1, 69.1, 240.1, 240.2, 172.1, 172.2, 93.1, 240.25; 424/93.1, 93.21, 93.2

[56] References Cited

U.S. PATENT DOCUMENTS

| 4,797,368 | 1/1989 | Carter et al. | 435/320.1 |
|---|---|---|---|
| 5,139,941 | 8/1992 | Muzyczka et al. | 435/325 |
| 5,478,745 | 12/1995 | Samulski et al. | 435/172.3 |

FOREIGN PATENT DOCUMENTS

| 0 488528 B1 | 6/1992 | European Pat. Off. . |
|---|---|---|
| 0 592836 A1 | 4/1994 | European Pat. Off. . |
| 4219626 A1 | 6/1992 | Germany . |
| WO 91/18088 | 11/1991 | WIPO . |
| WO 93/09239 | 5/1993 | WIPO . |
| WO9319660 | 10/1993 | WIPO . |
| WO 93/24641 | 12/1993 | WIPO . |
| WO9324641 | 12/1993 | WIPO . |
| WO 94/13788 | 6/1994 | WIPO . |
| WO9413788 | 6/1994 | WIPO . |

OTHER PUBLICATIONS

Marshall, Science, 269, 1995, 1050–1055.
Miller et al., FASEB J., 9, 1995, 190–199.
Culver et al., TIG, 10(5), 1994, 174–178.
Hodgson, Exp. Opin. Ther. Act., 5(50, 1995, 459–468.
Rojanasakul, Adv. Drug. Del. Rev., 18, 1996, 115–131.
NIH Report, Dec. 7, 1995, "Report and Recommendation . . . "pp. 1–40.
Hermonat et al., PNAS USA, 81, 1984, 6466–6470.
Goodman et al., Blood, 84(5), 1994, 1492–11500.
Buono et al., Gastroenterology, 106(4), 1994, A381 (Abstract).
Chang et al., Gastroenterology, 106(4), 1994, 1076–1084.
Soriano–Brucher, et al., (1991) "Gene Transfer into the Intestinal Epithelium" *Gastroenterology*, vol. 100, No. 5, Part 2, p. A252.
Adam Noel, et al., (1993) Enhancement of Gene Transfer Into Intestinal Epithelial Cell Lines (IEC–6 and RIE–1) By An Ecotropic Retroviral Vector, *Gastroenterology*, vol. 104, p. A269.
Friedmann, "Gene Therapy for Disorders of the CNS" *Gene Therapy*, 1(Supplement 1), pp. S47–S48 (Aug. 1993).
Hermonant and Muzyczka, "Use of Adeno–Associated Virus as a Mammalian DNA Cloning Vector: Transduction of Neomycin Resistance Into Mammalian Tissue Culture Cells", *Proc. Natl. Acad. Sci.*, 81:6466–6470 (Oct. 1984).
Lebkowski et al., "Adeno–Associated Virus: a Vector System for Efficient Introduction and Intergration of DNA Into a Variety of Mammamlian Cell Types" *Molecular and Cellular Biology*, 8(10):3988–3996 (Oct. 1988).

Laughlin et al., "Cloning of Infectious Adeno–Associated Virus Genomes in Bacterial Plasmids", *Gene*, 23:65–73 (1983).
McLaughlin et al., "Adeno–Associated Virus General Transduction Vectors: Analysis of Proviral Structures", *J. of Virology*, 62(6):1963–1973 (Jun. 1988).
Mendelson et al, "Expression and Rescue of a Nonselected Marker from an Integrated AAV Vector", *Virology*, 166:154–165 (1988).
Miller et al., "Factors Involved in Production Of Helper Virus–Free Retrovirus Vectos", *Somatic Cell and Molecular Genetics*, 12(2):175–183 (1986).
Ohi et al, "Construction and Characterization of Recombinant Adeno–Associated Virus Genome Containing Human Beta–Globin cDNA", *Journal of Cell Biology*, 107(6), Part 3, p. 304A, Abstract No. 1713 (Dec. 1988).
Ohi et al., "Construction and Replication of an Adeno–Association Virus Expression Vector that Contains Human β–Globin cDNA", *Gene*, 89:279–282 (1990).
Ohi et al., "Construction of Recombinant Adeno–Association Virus that Harbors Human Beta–Globin cDNA",*J. Cell. Biochem.*, Supplement 14A, Abstract D322 (1990).
Ohi et al., "Production and Expression of Recombinant Adeno–Assocated Viruses Harboring Human Beta–Globin cDNA", *FASEB J.*, 4(7):A2288, Abstract No. 3438 (1990).
Ohi et al., "Synthesis of a Human Beta–Globin in the Recombinant Adeno–Associated Virus–Infected Cells: Towards Gene Therapy of Hemoglobinopatheis", Experimental Hematology, 20(1):119, Abstract No. 56 (1992).
Ruffing et al., Assembly of Viruslike Particles by Recombinant Structural Proteins of Adeno–Associated Virus Type 2 in Insect Cells, *Journal of Virology*, 66(12):6922–6930 (Dec. 1992).
Samulski, "Adeno–Associated Virus–Based Vectors for Human Gene Therapy", *Gene Therapy From Laboratory to the Clinic*, Chapter 11, pp. 232–271 (1994),.
Samulski, "Adeno–Associated VIral Vectors", Virus in Human Gene Therapy, Chapter 3, pp. 53–76 (1995).
Samulski et al., "Cloning of Adeno–Associated Virus into pBR322: Rescue of Intact Virus from the Recombinant Plasmid in Human Cells" *Proc. Natl. Acad. Sci.*, 79:2077–2081 (Mar. 1982).
Samulski et al., "Helper–Free Stocks of Recombinant Adeno–Associated Viruses: Normal Integration Does Not Require Viral Gene Expression", *Journal of Virology*, 63(9):3822–3828 (Sep. 1989).
Samulski et al., "Rescue of Adeno–Associated Virus from Recombinant Plasmids:Gene Correction Within the Terminal Repeats of AAV", *Cell*, 33:135–143 (May 1983).

(List continued on next page.)

*Primary Examiner*—Bruce R. Campbell
*Attorney, Agent, or Firm*—Sughrue, Mion, Zinn, Macpeak & Seas, PLLC

[57] ABSTRACT

A method of expressing a gene product in the gut of an animal, which comprises administering a recombinant AAV vector to the gut of the animal, wherein the vector comprises a non-AAV gene of interest ligated into an AAV vector genome.

8 Claims, 2 Drawing Sheets

OTHER PUBLICATIONS

Samulski, "Targeted Integration of Adeno–Associated Virus (AAV) Into Human Chromosome 19", *EMBO J.,* 10(12):3941–3950 (1991).

Senapathy et al, "Replication of Adeno–Associated Virus DNA, Complementation of Naturally Occurring repMutants by a Wild–TYpe Genome or an oriMutant and Correction of Terminal Palindrome Deletions", *J. Mol. Biol.,* 178,179:1–20 (1984).

Shaughnessy et al, "Adeno–Associated Virus Vectors for MDR–1 Gene Therapy", *Proceedings of the American Association for Cancer Research,* 35:373, Abstract No. 2223 (Mar. 1994).

Sitaric et al, "Production of a Helper–Free Recombinant Adeno–Associated Virus that Harbors Human Beta–Globin cDNA", *FASEB J.,* 5(6):A1550, Abstracts Part III, Abstract No. 6843 (Mar. 1991).

Srivastava et al., "Construction of a Recombinant Human Parovurs B19: Adeno–Associated Virus 2 (AAV) DNA Inverted Terminal Repeats are Functional in an AAV–B19 Hybrid Virus", *Proc. Natl. Acad. Sci.,* 86:8078–8082 (Oct. 1989).

Tenenbaum and Hooghe–Peters, "Adeno–Associated Virus (AAV) as a Vector for Gene Transfer Into Glial Cells of the Human Central Nervous System", *Gene Therapy,* 1(Supplement 1), p. S80 (1993).

Tratschin et al, "A Human Parvovirus, Adeno–Associated Virus, as a Eucaryotic Vector: Transient Expression and Encapsidation of the Procaryotic Gene for Chlormphenicol Acetyltransferase", *Molecular and Cellular Biology,* 4(10):2072–2081 (Oct. 1984).

Tratschin et al, "Genetic Analysis of Adeno–Associated Virus: Properties of Deletion Mutants Constructed In Vitro and Evidence for an Adeno–Associated Virus Replication Function", *J. of Virology,* 51(3):611–619 (Sep. 1984).

Tratschin et al., "Adeno–Associated Virus Vector for High–Frequency Integration, Expression, and Rescue of Genes in Mammalian Cells" *Molecular Cellular Biology,* 5(11):3251–3260 (Nov. 1985).

Walsh et al, Gene Transfer and High Level Expression of a Human Gamma Globin Gene Mediated by a Novel Adeno–Associated Virus (AAV) Vector, *Clinical Research,* vol. 39, No. 2, Abstract No. 325A (1991).

Wong et al, "High Efficiency Gene Transfer Into Growth Arrested Cells Utilizing and Adeno–Associated Virus (AAV-)–Based Vector", *Blood,* 82(10) Supplement 1, p. 302a, Abstract No. 1195 (Nov. 1993).

Bosselman et al, "Replication–Defective Chimeric Helper Proviruses and Factors Affecting Generation of Competent Virus: Expression of Moloney Murine Leukemia Virus Structural Genes via the Metallothionein Promoter", Molecular and Cellular Biology, 7(5):1797–1806 (May 1987).

Carter, "Adeno–Associated Virus Vector", Current Opinion in Biotechnology, 3(5):533–539 (Oct. 1992).

Flotte et al, "Expression of the Cystic Fibrosis Transmembrane Conductance Regulator from a Novel Adeno–Associated Virus Promoter", J. Biol. Chem., 268(5):3781–3790 (Feb. 1993).

ORAL DELIVERY OR ADENO-ASSOCIATED VIRAL VECTORS

ACKNOWLEDGEMENTS

This invention was supported in part by NIH grants NS28227 and NS06208. The U.S. Government has rights in this invention as a result of this support.

INTRODUCTION

1. Technical Field

This invention is in the field of gene expression and is particularly directed to expression of gene products in the gut of an animal.

2. Background

Adeno-associated virus (AAV) vectors have been proposed and patented as vectors for expressing gene products in animals. See, for example, U.S. Pat. No. 5,193,941, issued Aug. 18, 1992, WO 9413788, as well as U.S. Ser. No. 08/227,319, the last application arising from the laboratory of the present inventor. A number of patents and other publications describe numerous AAV vectors and their uses, the uses generally being related to expression of gene products either in vitro (usually tissue cultures) or in vivo (usually in the lungs or oral mucosa, the normal sites of AAV infection, although U.S. application Ser. No. 08/227,319 abandoned, relates to expression in the central nervous system).

Investigations in the laboratory of the present inventor have surprisingly discovered that AAV vectors can act as effective, long-term expression systems in the gut of animals after oral ingestion. This discovery provides a new method of expressing desirable gene products and control elements in the gut of animals, including humans.

SUMMARY OF THE INVENTION

Accordingly, it is an object of the invention to provide new uses for AAV vectors that have already been developed for other purposes.

It is a further object of the invention to provide new recombinant AAV vectors containing gut-directed gene expression systems.

These and other objects of the invention have been accomplished by providing a method of expressing a gene product in the gut of an animal, which comprises administering a recombinant AAV vector to the gut of the animal, wherein the vector comprises a non-AAV gene of interest ligated into an AAV vector.

BRIEF DESCRIPTION OF THE DRAWINGS

The invention will be better understood by reference to the following detailed description of the invention when considered in combination with the drawings that form part of the specification, wherein.

DESCRIPTION OF SPECIFIC EMBODIMENTS

Figure 1A:
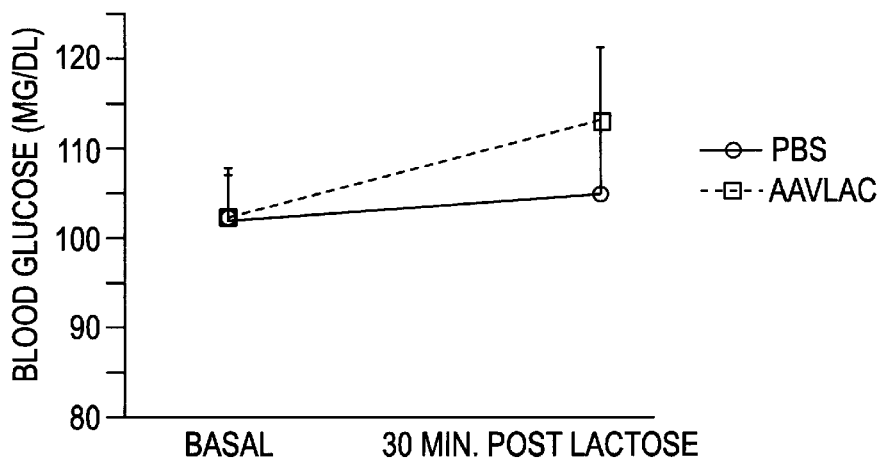
FIGS. 1A–1C are a graph showing plasma glucose and animal weight following an acute lactose challenge and a lactose-only diet. A. The change in plasma glucose following the ingestion of lactose in overnight fasted rats. Rats were studied 1 week following AAVlac or PBS administration. B. The oral lactose challenge was repeated after 14 days on the lactose diet. C. The weights of rats at baseline, 1 week and 2 weeks following a 14 day lactose and water diet. The diet commenced 1 week following oral AAVlac or PBS treatment.

The present invention is quite straightforward: prior to this invention recombinant AAV vectors were well known and were known to be able to transduce a number of cells and tissues, but had not been used or suggested for use in expressing gene products in the gut of animals. The invention therefore comprises administering to the gut of a target animal a recombinant AAV vector containing a gene whose expression is desired (along with the appropriate control elements, if desired or necessary in the normal manner for vectors). No new vectors are required, as previously known AAV vectors have been shown to work well for gut expression. Thus the invention is in part a discovery that no particular adaption of AAV vectors is required for gut expression, which is surprising in view of the strict requirements for AAV reproduction (i.e., presence of a helper virus) and the normal association of AAV with the lungs and nasal passages.

A number of scientific and patent publications describe the state of the art in the AAV vector field. Since no particular adaptations of prior art vectors are required for practice of the present invention, there is no need here to detail at great length the already well-known state of the art. However, the following publications are herein incorporated by reference, as are the patent and the patent applications (and their published equivalents) identified in the Introduction section of this specification, as these materials may be useful for those less experienced in the AAV field:

1. Samulski, R. J. et al. (1982) *Proc. Natl. Acad. Sci. USA.* 79:2077–2081 "Cloning of Adeno-Associated Virus into pBR322: Rescue of Intact Virus from Recombinant Plasmid in Human Cells"
2. Samulski, R. J. et al. (1983) *Cell* 33:135–143 "Rescue of Adeno-Associated Virus from Recombinant Plasmids: Gene Correction within the Terminal Repeats of AAV"
3. Laughlin et al. (1983) *Gene* 23:65–73 "Cloning of Infectious Adeno-Associated Virus Genomes in Bacterial Plasmids"
4. Hermanot, P. L. and Muzycka, N. (1984) *Proc. Natl. Acad. Sci. USA.* 81:6466–6470 "Use of Adeno-Associated Virus as a Mammalian DNA Cloning Vector: Transduction of Neomycin Resistance into Mammalian Tissue Culture Cells"
5. Senepathy, P. et al. (1984) *J. Mol. Biol.* 178, 179:1–20 "Replication of Adeno-Associated Virus DNA Complementation of Naturally Occurring rep⁻ Mutants by a Wild-type Genome or an ori⁻ Mutant and Correction of Terminal Palindrome Deletions"
6. Tratschin et al. (1984) *J. Virol* 51:611–619 "Genetic Analysis of Adeno-Associated Virus: Properties of Deletion Mutants Constructed In Vitro and Evidence for an Adeno-Associated Virus Replication Function"
7. Tratschin et al. (1984) *Mol. Cell. Biol.* 4:2072–2081 "A Human Parvovirus, Adeno-Associated Virus, as a Eukaryotic Vector: Transient Expression and Encapsidation of the Prokaryotic Gene for Chloramphenicol Acetyltransferase"
8. Miller et al. (1986) *Somatic Cell and Molecular Genetics* 12:175–183 "Factors Involved in Production of Helper Virus-Free Retrovirus Vectors"
9. Bosselman et al. (1987) *Mol. Cell. Biol.* 7:1797–1806 "Replication-Defective Chimeric Helper Proviruses and Factors Affecting Generation of Competent Virus: Expression of Moloney Murine Leukemia Virus Structural Genes via the Metallothionein Promoter"

10. Ohi et al. (1988) *J. Cell. Biol.* 107:304A "Construction and Characterization of Recombinant Adeno-Associated Virus Genome Containing β-globin cDNA"

11. McLaughlin et al. (1988) *J. Virol.* 62:1963–1973 "Adeno-Associated General Transduction Vectors: Analysis of Proviral Structures"

12. Lebkowski et al. (1988) *Mol. Cell Biol.* 8:3988–3996 "Adeno-Associated Virus: a Vector System for Efficient Introduction and Integration of DNA into a Variety of Mammalian Cell Types"

13. Samulski et al. (1989) *J. Virol.* 63:3822–3828 "Helper-Free Stocks of Recombinant Adeno-Associated Viruses: Normal Integration Does not Require Viral Gene Expression"

14. Srivastava et al. (October 1989) *Proc. Natl. Acad. Sci. U.S.A.* 86:20, 8078–82 "Construction of a recombinant human parvo virus-B19: adeno-associated virus-2 (AAV) DNA inverted terminal repeats are functional in an AAV-B19 hybrid virus—vector construction; potential application gene cloning in bone marrow cell culture and gene therapy"

15. Ohi, S. et al. (1990) *J.Cell.Biochem.* (Suppl.14A,D422) "Construction of recombinant adeno-associated virus that harbors human beta-globin cDNA—vector construction for potential application in hemoglobinopathy gene therapy; gene cloning and expression in 293 cell culture"

16. Ohi, S. et al. (1990) *Gene* 89 2:279–82 "Construction and replication of an adeno-associated virus expression vector that contains human beta-globin cDNA—plasmid PAVh-beta-GHP11 and plasmid PAVh-beta-G-psi-1 construction; potential application in gene therapy of e.g. sickle cell anemia or thalassemia"

17. Ohi, S. et al. (1990) *FASEB J.* 4:7, A2288) "Production and expression of recombinant adeno-associated viruses harboring human beta-globin cDNA—adeno-associated virus expression in 293 cell culture; potential gene therapy for hemoglobinopathy disease"

18. Samulski et al. (1991) *Embo J.* 10:3941–3950 "Targeted Integration of Adeno-associated virus AAV Into human chromosome 19"

19. Ruffing et al. (December 1992) *J. Virol.* 66:6922–6930 "Assembly of Viruslike Particles by Recombinant Structural Proteins of Adeno-Associated Virus Type 2 in Insect Cells"

20. Sitaric et al, (1991) *FASEB* 5:A1550 "Production of a Helper-free Recombinant Adeno-Associated Virus That Harbors Human β-globin cDNA"

21. Walsh et al. (1991) *Clin. Res.* 2:325 "Gene Transfer and High-level Expression of a human γ-globin Gene Mediated by a Novel Adeno-Associated Virus Promoter"

22. Carter, B. J. (October 1992) *Curr. Opinion in Biotechnol.* 3:533–539 "Adeno-Associated Virus Vectors"

23. Ohi et al. (1992) (Jun. 21–22, 1991) *EXP Hematol* 20 119 "Synthesis of a human beta globin in the recombinant adeno-associated virus-infected cells towards gene therapy of hemoglobinopathies"

24. Flotte et al. (1993) *J. B. C.* 268:3781–3790 "Expression of the Cystic Fibrosis Transmembrane Conductance Regulator from a Novel Adeno-Associated Virus Promoter"

25. Wong et al. (1993) *Blood* 82:302A. "High efficiency gene transfer into growth arrested cells utilizing an adeno-associated virus (AAV)-based vector"

26. Shaughnessey, et al. (1994) *Proc. Am. Assoc. Cancer Res.* 35:373 "Adeno-associated virus vectors for MDR1 gene therapy—multidrug-resistance gene cloning and gene transfer into hematopoietic stem cell culture using adeno-associated virus vector CWRSP for potential gene therapy"

27. Tenenbaum, L. et al. (1994) *Gene Ther.* (1, Suppl.1,S80) "Adeno-Associated Virus (AAV) as a Vector for Gene Transfer into Glial Cells of the Human Central Nervous System—Potential Gene Therapy"

28. Friedmann, T. (1994) *Gene Ther.* (1, Suppl. 1, S47–S48) "Gene Therapy for Disorders of the CNS—Parkinson Disease Alzheimer Disease Therapy by Gene Transfer Using Herpes Simplex Virus, Adeno Virus and Adeno-Associated Virus Vector"

29. DE 42 19626 A1 Assignee: Wehling, P. Filed: Jun. 16, 1992 Publication: Dec. 23, 1993 "Methods for Introducing Therapeutically Relevant Genes into Cells"

30. WO 91/18088 Assignee: Nat. Inst. Health-Bethesda Filed: May 17, 1991 (Priority May 23, 1990) Inventors: Chatterjee and Wong Publication: Nov. 28, 1991 "Adeno-Associated Virus (AAV)-based Eukaryotic Vectors"

31. EP 0 592 836 A1 Assignee: American Cyanamide Co. Filed: Sep. 16, 1993 (priority Sep. 17, 1992 U.S. 947127) Publication: Apr. 20, 1994 "Human Adeno-Associated Virus Integration Site DNA and use thereof"

32. WO 93/24641 Assignee: U.S. Dept. Health-Human-Serv. Filed: Jun. 2, 1993 (Priority Jun. 2, 1992) Publication: Apr. 20, 1994 "Adeno-Associated Virus with Inverted Terminal Repeat Sequences as Promoter"

33. WO 93/09239 Assignee: Res. Corp. Technol. Filed: Nov. 6, 1992 (U.S. priority Nov. 8, 1991) Publication: May 13, 1993 "Adeno-Associated Virus-2 Basal Vectors"

34. EP 0 488 528 A1 Assignee: Appl. Immune Sci. Filed: Oct. 29, 1991 (U.S. priority Oct. 30, 1990) Publication: Jun. 3, 1992 "Recombinant adeno-associated Virus Vectors"

35. U.S. Pat. No. 4,797,368 Assignee: U.S. Dept. Health-Human-Serv. Filed: Mar. 15, 1985 Issued: Jan. 10, 1989 "Adeno-associated Virus as Eukaryotic Expression Vector"

Two recent review article provide a particularly complete overview of the recent status of gene therapy using AAV virus and include a collection of additional recent scientific publications in this field.

36. Samulski, R. J. "Adeno-associated Viral Vectors"Chapter 3 in "Viruses in Human Gene Therapy" Chapman & Hall, J.-M. H. Vos., ed.

37. Samulski, R. J. "Adeno-associated Virus-based Vectors for Human Gene Therapy"Chapter 11 in "Gene Therapy: From Laboratory to the Clinic" World Scientific, K. M. Hui, ed.

Actual delivery of the viral vector for purposes of the invention is accomplished by using any physical method that will transport the AAV recombinant vector to the gut. In this discussion on administration, "AAV vector" means both a bare recombinant AAV DNA vector or AAV vector DNA packaged into viral capsids. Simply dissolving an AAV vector in phosphate buffered saline has been demonstrated to be sufficient for useful gut expression, and there are no known restrictions on the carriers or other components that can be coadministered with the vector (although compositions that degrade DNA should be avoided in the normal manner with vectors). Pharmaceutical compositions can be prepared as oral tablets, capsules, or ingestible liquids or as suppositories. The vectors can be used with any pharmaceutically acceptable carrier for ease of administration and handling.

The AAV vector may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the AAV vector may be incorporated with excipient and used in the form of ingestible tablets, buccal tablets, troches, capsules, elixirs, suspensions, syrups, wafers, and the like. Such compositions and preparations should contain at least 1 µg, preferably 10–1000 µg of AAV vector DNA, or $5 \times 10^3$ to $5 \times 10^6$ infectious units AAV vector per kg body weight. The amount of AAV vector in a therapeutically useful composition is that which is sufficient to produce gene expression at a therapeutically useful level. Preferred compositions or preparations according to the present invention are prepared so that an oral dosage unit form contains between about 10 and 1000 µg of AAV vector DNA or $10^4$ to $10^6$ infectious units AAV vector.

The tablets, troches, pills, capsules and the like may also contain the following: a binder such as polyvinylpyrrolidone, gum tragacanth, acacia, sucrose, corn starch or gelatin; an excipient such as calcium phosphate, sodium citrate and calcium carbonate; a disintegrating agent such as corn starch, potato starch, tapioca starch, certain complex silicates, alginic acid and the like; a lubricant such as sodium lauryl sulfate, talc and magnesium stearate; a sweetening agent such as sucrose, lactose or saccharin; or a flavoring agent such as peppermint, oil of wintergreen or cherry flavoring. Solid compositions of a similar type are also employed as fillers in soft and hard-filled gelatin capsules; preferred materials in this connection also include lactose or milk sugar as well as high molecular weight polyethylene glycols. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the AAV vector, sucrose as a sweetening agent, methyl and propylparabens as preservatives, a dye, flavoring such as cherry or orange flavor, emulsifying agents and/or suspending agents, as well as such diluents as water, ethanol, propylene glycol, glycerin and various like combinations thereof. Of course, any material used in preparing any dosage unit form should be pharmaceutically pure and substantially non-toxic in the amounts employed. In addition, the AAV vector may be incorporated into sustained-release preparations and formulations.

Since AAV has in the past been shown to have a broad host range (for pulmonary expression) and has now been demonstrated to be operable in the gut, there are no known limits on the animals in which gut expression can take place, although expression in animals with evolutionarily developed small and large intestines is preferred, particularly in mammals, birds, fish, and reptiles, especially domesticated mammals and birds such as cattle, sheep, pigs, horses, dogs, cats, chickens, and turkeys. Both human and veterinary uses are particularly preferred.

The gene being expressed can be either a DNA segment encoding a protein, with whatever control elements (e.g., promoters, operators, ribosome binding sites) are desired by the user, or a non-coding DNA segment, the transcription of which produces all or part of some RNA-containing molecule or anti-sense molecule that is functional in cells. Since the present invention is directed to a route of delivery and to the vector rather than to the material being delivered, there are no limitations on the foreign DNA (non-AAV DNA) being delivered by the vector. While delivery of genes associated with correction of genetic deficiencies related to gut expression is preferred, expression of genes in the gut has the capability of correcting aberrant gene expression in other locations as a result of transport of expression products throughout the body.

We have demonstrated the invention by correcting lactase deficiency in the gut. We used a recombinant adeno-associated virus (AAV) expressing β-galactosidase (AAVlac) and delivered the vector to the proximal intestine using a peroral route. Lactase-deficient rats that received AAVlac were able to metabolize an acute lactose load as demonstrated by a rise in plasma glucose. In contrast, phosphate-buffered saline(PBS)-treated controls demonstrated no effect of lactose on plasma glucose. Furthermore, when animals were placed on a restricted, lactose-only diet, PBS-treated rats continued to lose weight over the entire 2-week test-diet period. In contrast, AAVlac-treated animals had no weight loss during the second week. PCR and RT-PCR and histological analysis confirmed intestinal persistence of viral DNA and expression of the vector-encoded β-galactosidase for the life of the animal (extending to 6 months). Moreover, when animals were re-challenged with a lactose load at 3 months after a single AAVlac or PBS treatment, AAVlac animals retained their ability to metabolize lactose and maintained body weight on a lactose diet. These data indicate that oral delivery of an AAV vector can result in long-lasting phenotypic correction of lactase deficiency.

This demonstration system was selected both to prove the principle of the invention and to demonstrate the invention in a therapeutically useful mode. Adult-type hypolactasis is genetically determined by an autosomal recessive gene (Sahi et al. Lancet 1973 2:823–828). It is the world's most common genetic disorder, afflicting over 50% of the world's population ranging from 100% in some Southeast Asian populations to less than 5% in some Northern European countries (Flatz Human Genet. 1984 36:306–310). Although the symptoms associated with lactose intolerance are relatively mild and readily controlled by omitting lactose-containing foods, there is some debate as to the potential clinical significance of the dietary restrictions which typically accompany lactose intolerance. Specifically, the reduction in calcium-intake associated with complying with a lactose-free diet may lead to an acceleration in the loss of bone mass in the elderly (Flatz 1987 Advances in Human Genet. 16:1–77 New York Plenum Press); and in adolescents and young adults, it may reduce the bone mineral mass (Mobassaleh et al. Pediatrics 75:160–166 1985).

We elected to study lactase deficiency in the rat as a model of a gastrointestinal genetic disease. We were particularly interested in determining whether we could obtain phenotypic correction using an orally delivered viral vector. We have previously shown that AAV vectors can result in long-term transgene expression in terminally differentiated cells following in vivo administration (Birge et al. NEJM 1967 276:445–448). AAV has several features which make it particularly attractive for gene therapy. It is a defective, helper-dependent virus, and the wild-type is non-pathogenic. Vectors can be generated which are completely free of helper virus (Bayless et al. 1975 NEJM 292:1156–1159). Furthermore, some recombinant AAV vectors retain just 145 base terminal repeats with the entire coding sequences removed. In other AAV vectors, non-AAV DNA is operably linked to a vector comprising a double-D AAV genomic segment consisting of 165 basepairs including an internal terminal repeat with D segments at both ends. These vectors therefore are devoid of all viral genes, minimizing any possibility of recombination and viral gene expression.

Moreover, unlike adenovirus, they do not appear to elicit any immune response. Another feature of AAV which makes it potentially suitable for an orally based vector is that of hardiness—AAV is resistant to temperature, pH extremes and solvents (Sandler et al. Am. J. Clin. Nutr. 1985 42:270–274). Furthermore, during an active infection in humans, wild-type AAV is typically found in both respiratory tract and gastrointestinal secretions, the gut is therefore a normal host tissue for the virus.

Lactose intolerance is most commonly associated with a reduction in intestinal lactase activity. Lactose digestion is dependent on the enzyme, lactase-phlorizin hydrolase (LPH), a microvillar protein which has both galactosidase activity and glycosyl-N-acylsphingosine glucohydrolase activities. However, dietary administration of yeast or bacterial β-galactosidase is sufficient to confer the ability to metabolize lactose (Kaplitt et al. Nature Genet. 1994 8:148–154).

Most mammalian species are relatively lactase deficient following weaning, although this developmental change in LPH expression does not appear to be simply a reduction in gene transcription. In both humans and rats, although LPH mRNA declines after weaning, it reappears during adulthood. However, this increase in mRNA is not associated with an increase in translation; and adult enzyme levels within the brush-border remain low. It appears that some LPH protein is expressed, but the enzyme is accumulated within the golgi region and is not transported to the brush-border. Based on this information, we conducted the following examples to illustrate the invention. These examples are not to be considered limiting of the invention unless so specified.

EXAMPLES

We decided to demonstrate increased enterocyte expression of β-galactosidase using a viral vector and to obtain brush-border increases in enzyme activity resulting in phenotypic correction in an animal model. We elected to study the adult rat as a genetic model of adult-onset hypolactasia. However, upon screening adult (>4-month-old) Sprague-Dawley and Fisher rats, a significant number (at least 70%) had persistent lactase activity as determined by a rise in plasma glucose following an oral lactose challenge test. We therefore selected only those animals that had a flat plasma glucose curve following feeding with lactose.

Rats were randomized to receive AAVlac or vehicle. The vector (or PBS vehicle) was delivered in lightly anesthetized, fasting rats using an oro-gastric tube. Animals were allowed to recover and placed on a regular rat chow diet. At various times following AAVlac administration, animals were challenged with lactose and plasma glucose samples measured. Moreover, at one week following AAV and again at 120 days, animals were put on a lactose-only diet. Animal weights were monitored, and the lactose challenge was repeated.

AAVlac DNA persistence and expression was determined using PCR and RT-PCR, in situ RT-PCR and X-gal immunohistochemistry. No β-galactosidase (as determined using X-gal staining) expression was observed within the first 3 hours. However, at 6 hours, clear blue (X-gal positive) cells were seen in a characteristic distribution. Moreover, this expression persisted throughout the animals' lifetime with no loss of expression observed. In contrast to the endogenous enzyme activity in lactase-plus animals which is at the tips of the villi and in the brush-border, the vast majority of expression was within the lamina propria, even at 6 hours following peroral administration. On high-power magnification, however, it appeared that some of the enzyme diffused or was transported to the intestinal brush-border.

Figure 1B:
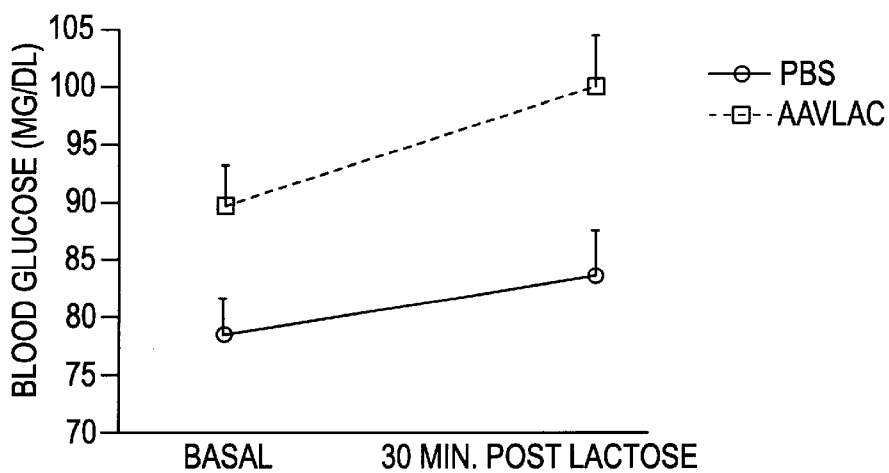
Figure 1C:
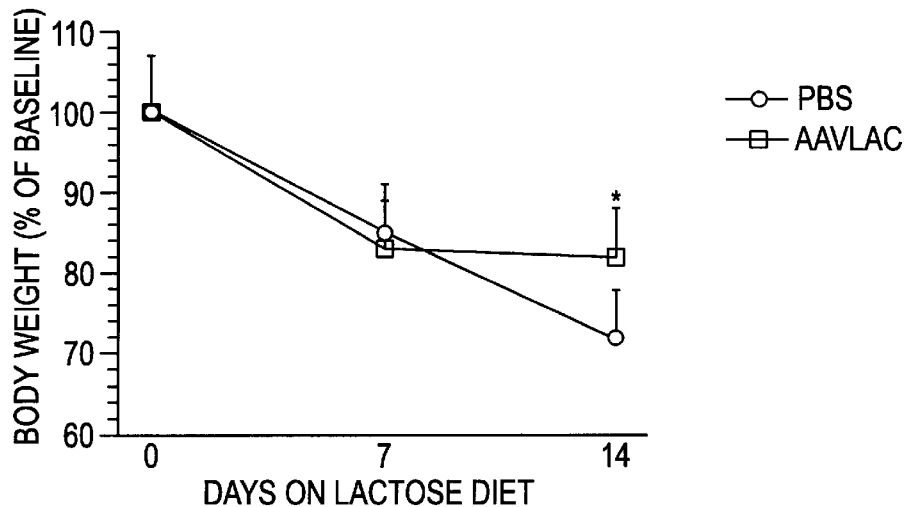

Administration of AAVlac did not effect the weight gain or behavior of any rats fed on regular rat chow. However, on changing to the lactose-only diet, both AAVlac and PBS-treated rats lost weight. Over the first week, this weight loss was identical in both groups and largely reflected a reduction in food intake and a lack of interest in ingesting the lactose. However, in the second week, both groups ingested the lactose. Of interest, the AAVlac animals had no further weight loss; whereas, the PBS-treated animals continued to lose weight at the same rate as over the first week. Moreover, following a lactose challenge, the AAVlac animals had a significant elevation in plasma glucose; whereas, the plasma glucose level of the PBS-treated animals remained flat (FIG. 1).

Figure 2A:
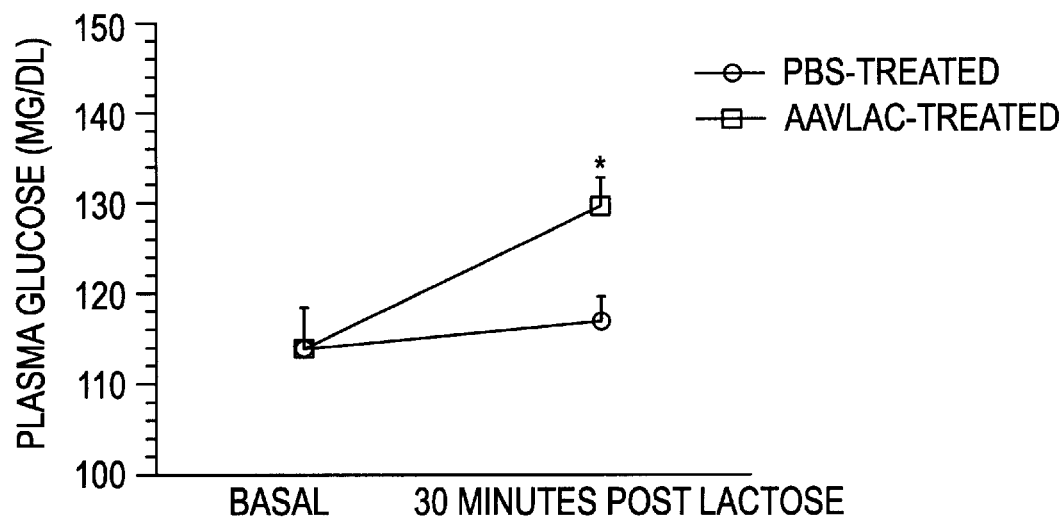
FIGS. 2A–2B. A. The change in plasma glucose following the ingestion of lactose in overnight fasted rats, which were challenged 120 days following a single peroral dose of AAVlac or PBS. B. The weights of rats at baseline, 1 week and 2 weeks following a 14 day lactose and water diet. The diet commenced 120 days following oral AAVlac or PBS treatment.
Figure 2B:
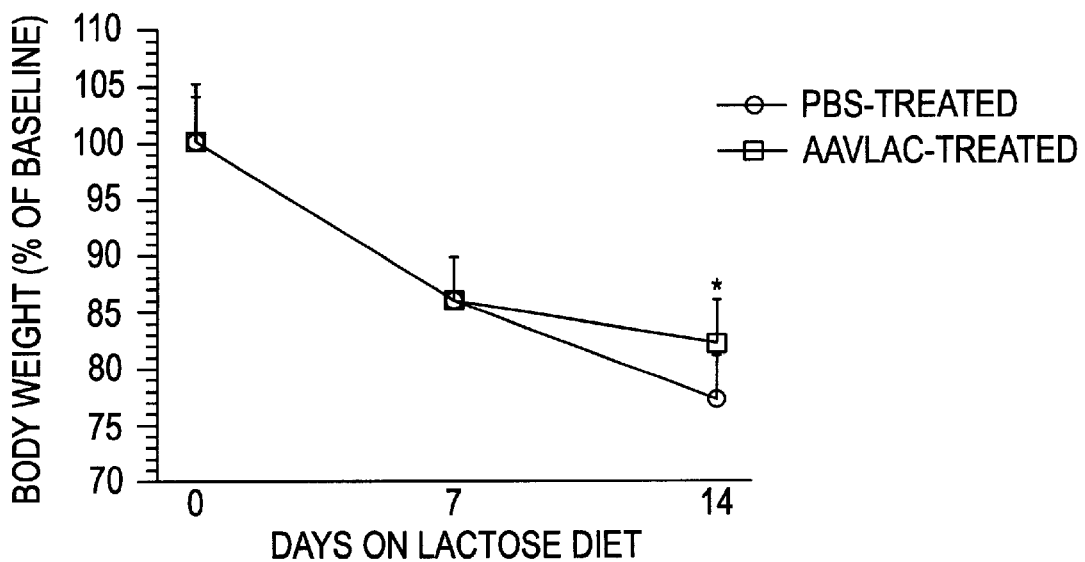

A group of animals was followed for 4 months following a single oral administration of the vector. At 120 days these rats were rechallenged with a lactose load and then recommenced on a lactose-only diet. In a manner similar to the challenge during the first week following AAVlac administration, the vector-treated animals increased plasma glucose whereas the controls had no response. Furthermore, the PBS-treated animals had persistent weight loss on the lactose diet, whereas the AAVlac-treated animals were able to maintain body weight during the second week (FIG. 2).

Experimental Details

Adult (age>4 months), male Fisher 344 rats were screened using an oral lactose challenge. Rats were fasted overnight. On the morning of the test, a baseline, fasting plasma glucose level was taken from blood obtained from the tail vein. The animals were then administered 2 gr lactose and the plasma glucose was again measured in a tail vein sample at 30 minutes. Plasma glucose was measured suing a Beckman Glucose Analyzer II as previously described (During M J et al. J Clin Invest 1995; 95:2403–2408). Rats which had an increase in plasma glucose of greater than 5 mg/dl were excluded from further study. Rats with flat ($\Delta$<5 mg/dl) were randomized to 2 groups: A) AAVlac and B) PBS. Rats randomized to AAVlac were lightly anesthetized with ketamine/xylazine (8/80 mg/kg i.p.) and an oro-gastric tube inserted. 10 microliters of AAVlac (titer $5 \times 10^6$/ml in a carrier solution or 0.5 ml PBS or PBS alone was infused. Rats were allowed to recover and returned to ad libitum access to water and rat chow. AAVlac is the recombinant AAV vector prepared from pAB II as described (Goodman et al. Blood 1994 84:1492–1500).

Rats were fasted overnight, and blood was taken by nicking the tail vein. Rats were then given a 30 minute access to 2 gram of lactose (Sigma, St. Louis) in their home cages. Thirty minutes from the midpoint of the lactose meal, a second tail vein sample was taken. The blood was immediately centrifuged upon collection and the plasma analyzed for glucose using the Beckman glucose analyzer. In preliminary studies we had determined that a forced oral dose of lactose using either an orogastric or other forced feeding resulted in a highly variable stress hyperglycemic response. Moreover, eating behavior per se was insufficient to raise plasma glucose.

Rat chow was removed from housing cages and was replaced with 100% lactose (Sigma, St. Louis). Ad libitum water access was continued at all times. Animals were weighed at the beginning and at 7 days and 14 days after commencement of the lactose diet. At the end of 14 days, the lactose was removed and the rats were fed regular rat chow.

These studies demonstrate the feasibility of administering an AAV vector orally to obtain long-term gene expression. Moreover, there was no loss of expression evidenced over a 6-month period, and phenotypic correction extended to at least 4 months.

In normal rats, LPH expression is observed within the enterocytes with the protein transported to the brush-border. The expression of β-galactosidase in our study was somewhat atypical in that expression was most apparent in the lamina propria, with little expression in enterocytes. As turnover of enterocytes occurs every 3–5 days, it might be expected that after 4 or 5 days expression would not be seen within this population of cells. Alternatively, a few progenitor cells in the crypts may have been transduced, although we did not observe any persistent gene expression in enterocytes at both the tips of the villi or in the depths of the crypts. In contrast, as early as 6 hours following AAVlac administration, expression was observed within the lamina propria. This finding is consistent with the function of M cells within the gut. M cells are specialized gut epithelial cells which are scattered throughout the intestine but are found most concentrated overlying Peyers patches and clusters of immune cells. M cells essentially scavenge foreign proteins, viruses and bacteria and rapidly (within 3 hours) transport these foreign agents to the immune cells within the lamina propria. The early expression of vector encoded β-galactosidase within the lamina propria is consistent with this pathway. In high powered sections we were able to see enzyme activity (as demonstrated by X-gal staining) extending down through the enterocytes to the brush border, thus contributing to the phenotypic correction we observed in this model. However, the greatest expression was within the lamina propria. The gut antigen presenting cells (APC) may be the best cells to generate systemic immune responses and are a target for vaccine development (Berns et al. Adv. Virus Res. 1979 25:407–409). Oral AAV vectors may therefore be very attractive choice for immunization. The persistent expression within the vascular lamina propria also suggest this route may be applicable for protein replacement, particularly where release into the portal circulation is desired. For example, this approach may be useful for restoration of portal insulin release in diabetes mellitus. The stable expression of a transgene within the gastrointestinal immune system may also be useful to generate immune tolerance akin to oral antigen approaches (Scrimshaw et al. Am. J. Clin. Nutr. 1988 48:1129–1136).

In summary, we have demonstrated that a single peroral administration of an AAV vector can result in persistent expression and long-lasting phenotypic correction. Our data indicates that a "gene in a tablet" strategy using AAV vectors will be useful for a broad range of conditions. Moreover, the lack of toxicity and non-invasiveness of this approach will render oral AAV vectors as a palatable choice compared to current pharmacological treatments.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of obtaining production of a protein in cells of the small intestine of an animal, which comprises:
   orally administering an encapsidated recombinant adeno-associated virus (AAV) DNA vector to said animal, wherein said recombinant AAV DNA vector comprises a promoter operably linked to a non-AAV DNA encoding said protein, and wherein said recombinant AAV DNA vector is packaged into an AAV capsid.

2. The method of claim 1, wherein said vector is administered dissolved or suspended in a liquid pharmaceutically acceptable carrier.

3. The method of claim 2, wherein said liquid carrier comprises an aqueous solution.

4. The method of claim 1, wherein said vector is administered in a solid pharmaceutically acceptable carrier.

5. The method of claim 1, wherein said vector comprises non-AAV DNA ligated into an AAV genome in place of or in addition to an AAV DNA sequence excluding the first and last 145 basepairs of said AAV genome or non-AAV DNA operably linked to a vector comprising a double-D AAV genomic segment consisting of 165 basepairs including an internal terminal repeat with D segments at both ends.

6. The method of claim 1, wherein said animal is a bird or mammal.

7. The method of claim 1, wherein said animal is a human.

8. The method of claim 1, wherein said DNA encoding said protein comprises a β-galactosidase gene.

* * * * *